United States Patent [19]
Kelman

[11] Patent Number: 4,648,879
[45] Date of Patent: Mar. 10, 1987

[54] POSTERIOR CHAMBER INTRAOCULAR LENS

[76] Inventor: Charles D. Kelman, 269 Grand Central Pkwy., North Shore Towers, Floral Park, N.Y. 11005

[21] Appl. No.: 798,986

[22] Filed: Nov. 18, 1985

[51] Int. Cl.⁴ .............................................. A61F 2/16
[52] U.S. Cl. ......................................................... 623/6
[58] Field of Search ............................................ 623/6

[56] References Cited

U.S. PATENT DOCUMENTS

| | | | |
|---|---|---|---|
| 4,172,297 | 10/1979 | Schlegel | 623/6 |
| 4,495,665 | 1/1985 | Kelman | 623/6 |
| 4,562,600 | 1/1986 | Ginsberg et al. | 623/6 |

FOREIGN PATENT DOCUMENTS 0128784  12/1984  European Pat. Off. ............... 623/6

OTHER PUBLICATIONS

Medical Optics PC-15L, Posterior Chamber Intraocular Lens (advertisement), American Medical Optics, Oct. 1983.

Primary Examiner—Ronald L. Frinks
Attorney, Agent, or Firm—Henry Sternberg

[57] ABSTRACT

A posterior chamber intraocular lens having, according to one preferred form, at least one projection extending rearwardly from a location radially outwardly of a peripheral rear edge portion of the optic for spacing, from the mid-portion of the rear surface of the optic, the adjacent region of the posterior capsule containing the tension line. If desired, after implantation of the lens, the posterior capsule may be safely perforated with a laser beam transversely to a line of tension formed by the projection, causing the posterior capsule to tear and form an opening to eliminate any cloudiness of the posterior capsule from behind the optic. According to another preferred form, the lens has a pair of rearward projections, each located radially outwardly of opposite peripheral portions of the optica and cooperating to produce a similar tension and spacing effect.

10 Claims, 5 Drawing Figures

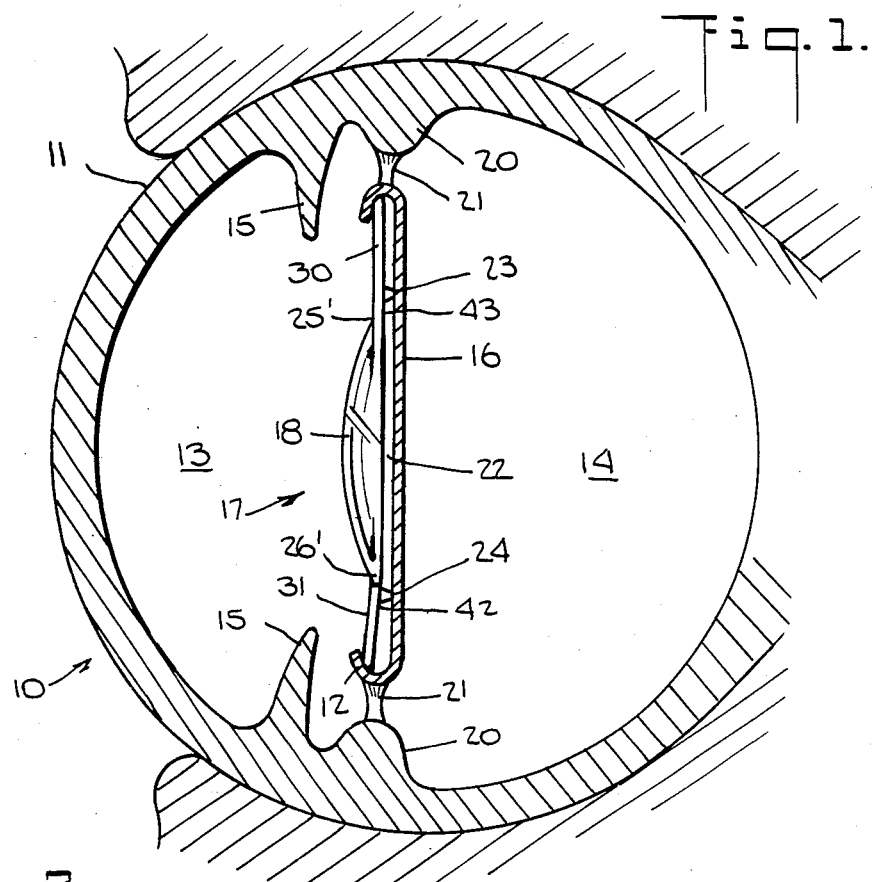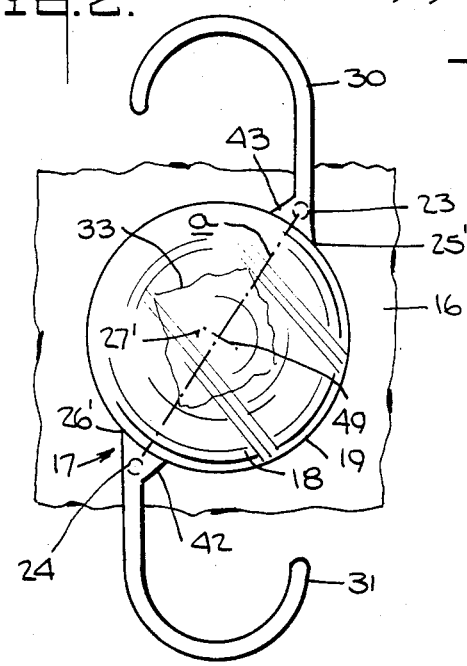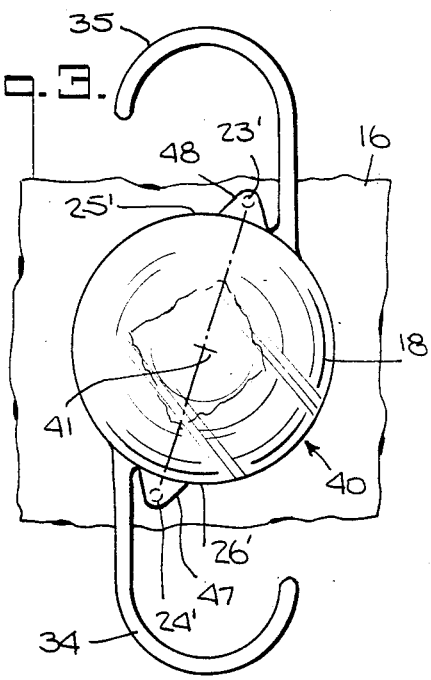

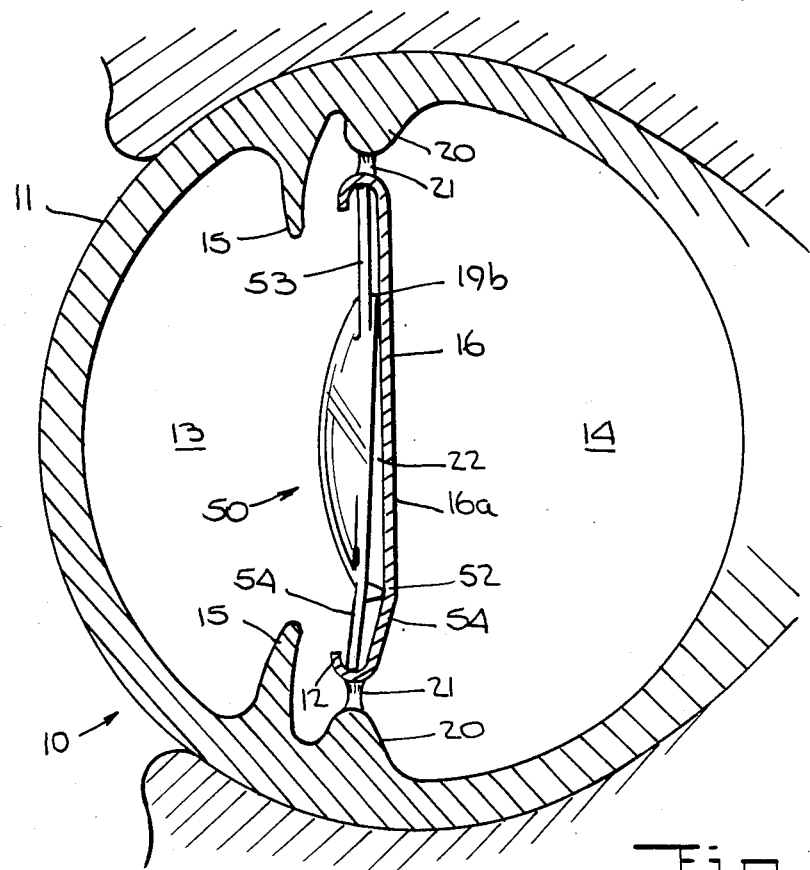
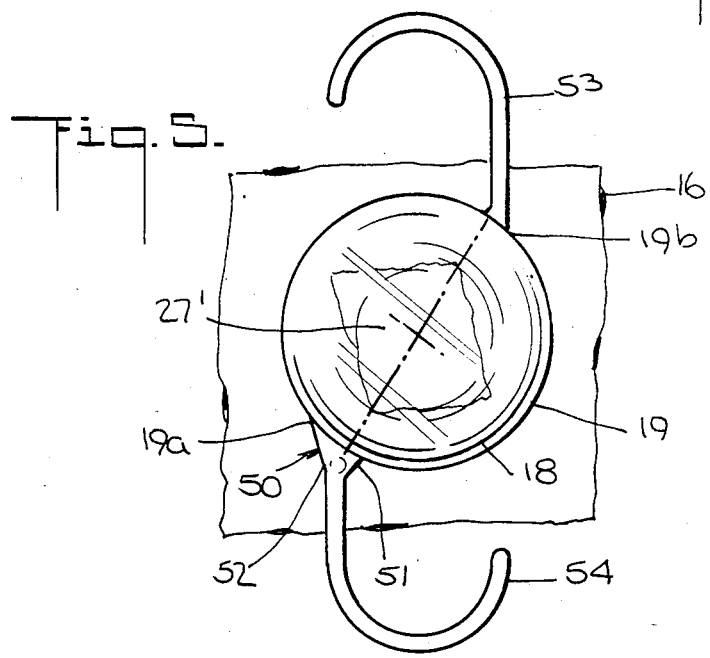

POSTERIOR CHAMBER INTRAOCULAR LENS

This invention relates to posterior chamber intraocular lenses and more particularly to posterior chamber lenses of the type having a lens body or optic positioned in the capsule of the eye.

After an intraocular lens has been implanted in an eye following the removal of a natural lens by extracapsular surgery, the posterior capsule which remains in the eye may at some later time become clouded and require an opening to be made therein for clear vision. A laser beam may be used to make successive perforations in the posterior capsule, which perforations typically join together to form the desired opening.

It is known to provide posterior chamber intraocular lenses with projections extending rearwardly from the rear face of the optic, see, for example, my U.S. Pat. No. 4,495,665, for contacting the posterior capsule and forming stress lines therein for facilitating laser surgery. It is also known to provide an annular lip on the rear surface of the lens body for spacing the remaining portions of such rear surface from the posterior capsule for permitting the insertion of surgical instruments between the capsule and the lens body, see, for example, the patent to Hoffer, U.S. Pat. Re. No. 31,626.

In both these examples, the pointed projections on the one hand, and the annular projections, on the other hand, the spacing means are located on the rear face, proper, of the optic portion of the lens, and are thus in a position to interfere with the light rays being focused on the retina by the optic.

By virtue of their location, directly on the rear face of the lens body, such projections or lip, may reduce the amount of light impinging on the retina, may result in some distortions in vision, and/or may result in glare.

The foregoing possible disadvantages become even more of a problem with the ever increasing quest for decreasing the size of the optic in intraocular lenses. Now that lenses are contemplated with optics which are no more than 3 mm in diameter, the above disadvantages of spacer projections located on the rear face of such small optic, take on a much greater significance than before.

In accordance with one preferred embodiment of the present invention, a posterior chamber intraocular lens comprises a lens body, a pair of position-fixation means extending from generally diametrically opposed regions of the lens body for positioning the lens body in the posterior capsule of an eye and each such position-fixation means including a rearwardly projecting projection adapted to contact the posterior capsule. The position-fixation means cooperate to press the projections against the posterior capsule, after seating of the lens in the eye, to produce a tension line in the posterior capsule in the region between the projections, sufficient to tear the posterior capsule after perforation of the capsule in said region and sufficient also, to space the central region of the rear surface of the lens body from the posterior capsule a distance sufficiently large to safely allow a subsequent laser capsulotomy.

In accordance with a second preferred embodiment of the invention, a posterior chamber intraocular lens intended for implantation in the capsule of an eye after extracapsular extraction, comprises a medial, light-focusing, lens body having a rear face, position-fixation means cooperating with the lens body, for centering the lens within the chamber, a pair of tab means extending generally radially from opposite peripheral portions of the lens body and integral therewith, a pair of projections respectively integral with the tab means at locations thereon closely adjacent to but radially outward of such opposite peripheral portions, respectively, of the lens body and extending rearwardly behind the plane containing the rear face of the lens body. The position-fixation means are adapted to press the projections against the posterior capsule for spacing a central portion of the posterior capsule away from the rear face a distance sufficiently large to safely allow a subsequent laser capsulotomy.

According to a third preferred embodiment, a lens is provided with a single rearward projection outwardly of one peripheral edge portion of the lens body, or optic, for forming stress lines between that projection and the opposite peripheral edge portion of the rear face of the lens. The position-fixation members cooperate to press the projection, on the one hand, and the opposite peripheral edge of the lens body, on the other hand, against the posterior capsule for forming such stress line and for spacing portions of the rear face of the optic a sufficient distance from the capsule to safely allow laser capsulotomy.

Further objects and advantages of the present invention will be apparent to those skilled in the art to which it relates from the following detailed description thereof made with reference to the accompanying drawings forming a part of this specification.

BRIEF DESCRIPTION OF THE DRAWINGS

FIG. 1 is a fragmentary sectional view illustrating a first preferred embodiment of the lens of the present invention within the posterior chamber capsule;

FIG. 2 is an elevational view of the lens in accordance with the FIG. 1 embodiment of the present invention, within the posterior capsule;

FIG. 3 is an elevational view illustrating a second preferred embodiment of the lens of the present invention within the posterior chamber capsule;

FIG. 4 is a fragmentary sectional view illustrating another preferred embodiment of the lens of the present invention in the posterior chamber;

FIG. 5 is a front elevational view of the lens according to the FIG. 4 embodiment.

Referring now more particularly to FIG. 1 of the drawings, a human eye 10 is represented in section, with portions omitted for the sake of clarity. The eye 10 includes a cornea 11. Anterior chamber 13 and posterior chamber 14 are defined by the position of the iris 15. A membrane or posterior capsule 16 supports a lens 17 constructed in accordance with the invention and implanted by the surgeon after the anterior capsule (only a small portion 12 of which remains) and natural lens (not shown) which may have had a cataract therein, were removed surgically. The capsule 16 is normally connected to the ciliary body 20 by a plurality of zonules 21.

The lens 17 includes a lens body 18 having a rear surface 22 having diametrically opposed peripheral portions 25' and 26' and a mid-portion 27'. The lens body 18 preferably has a substantially circular periphery 19.

The lens of FIGS. 1 and 2 includes position-fixation means comprising two members extending from the lens body 18 for positioning the lens body in the capsule of an eye.

Position-fixation members 30, 31 may be of conventional construction, each however preferably having a reinforced connecting portion 42, 43 adjacent the periphery 19 of the lens body 18, and each having, on the rear surface of the respective connecting portion, a rearward projection 23, 24, respectively. Preferably, the projections 23 and 24 are pointed (slightly rounded at the tip) and define, at their tips, substantially individual points spaced rearwardly of the rear surface 22 of the lens body 18. Each projection 23, 24 preferably has a maximum dimension in a direction parallel to said rear surface of not greater than 1 millimeter. Preferably, also, the length of each of the projections 23 and 24 in a direction rear-wardly from said rear surface is in the range of between about 1 to 2 millimeters. The term "tab" or "tab means" is intended to include both a seperate tab such as tabs 47, 48 in FIG. 3 and the reinforced connecting portion of the haptic, such as elements 42 and 43 of FIG. 2.

The position-fixation members 30 and 31 may be of conventional construction but preferably are at a slight forward angle with respect to the plane of the rear surface 22 of the lens body 17 to augment the pressing of the projections 23 and 24 against the posterior capsule 16, as seen in FIG. 1.

The projections 23 and 24 are effective to cause a substantially concentrated line of tension along the posterior capsule, in the region between the projections, sufficient to tear the posterior capsule after limited laser perforation of the capsule in said region. Such tear, as a result of the tension line, is substantially greater in size than would otherwise be expected to result from limited laser perforation alone. In other words, fewer laser perforations are required to accomplish the same size opening in the posterior capsule. Furthermore, the pressure exerted by the pair of projections on the posterior capsule causes at least a strip-shaped portion of the capsule 16, extending between said projections, to be spaced from said rear face 22 of the lens body by a distance sufficient to permit a subsequent safe laser capsulotomy. A spacing of only about ½ to 1½ millimeters is desireable.

Referring now more particularly to FIG. 3 of the drawings, there is represented a lens 40 similar to the lens 17 and having an optical axis 41. The lens 40 also includes at least two projections 23' and 24' similar to the projections 23 and 24 of the lens 17 and spaced at substantially equal distances from the optical axis 41. The projections 23' and 24' may, for example, be spaced from the periphery of lens body 44 by a distance to their tips, of approximately 1 millimeter and preferably are located on generally triangularly shaped tabs 47 and 48 extending radially outwardly from generally opposite peripheral regions 25' and 26', respectively, of the lens body, or optic, 18.

In both FIGS. 2 and 3 a fragmentary portion of the posterior capsule 16 is represented behind the lens.

Referring again to FIGS. 1 and 2, after the lens 17 is implanted a, line of tension will be formed in the posterior capsule 16 between the pair of projections 23 and 24 generally corresponding to the broken-line represented by reference letter a on the drawing. If it is desired at some time after implantation of the lens to open the central region of the posterior capsule, the surgeon may perforate the posterior capsule 16 with a laser beam in one or more directions transverse to the line of tension a, with such perforations crossing the line of tension, causing the posterior capsule to tear to form an opening 33 in the posterior capsule 16. An imaginary line along which laser perforations may, for example, be made is represented by broken line 49.

The haptics 34 and 35 of FIG. 3 are substantially the same as haptics 30 and 31 of FIG. 2 except that haptics 30 and 31 are connected to the lens body via triangularly shaped tab means 42, 43 extending radially outwardly from and integral, preferably unitary, with opposite peripheral portions of the lens body 18. The projections 23 and 24 are, in the FIG. 2 embodiment located on and extend rearwardly from the tab means 42, 43. It will be understood that while preferably the tabs 42, 43 are merely extension of and form part of the haptics 30, 31 these tabs, with the rearward projections thereon could be independent of the haptics and could, for example, be located as shown in FIG. 3, peripherally adjacent to the haptics 34, 35, respectively. The tabs 47 and 48, of FIG. 3 are peripherally adjacent to, but may be slightly spaced from, the haptics 34, 35. Rearwardly extending projections 23' and 24' are preferably unitary with the tabs 35 and 34, respectively, and are otherwise in position and shape similar to the tabs 23 and 24. Preferably, the tabs 47 and 48 as well as the tabs 42 and 43 are translucent (or opaque) to the passage to light therethrough, so that the risk of glare will be avoided. This is preferably accomplished by roughening the front and or rear surface of the tabs. It will also be understood that the haptics 30, 31 and 34, 35 have been depicted, for illustrative purposes only, as simple J-shaped members. Actually, conventional haptics of many different varieties, suitable for posterior chamber lenses, can be used with the present invention.

According to a still further embodiment of the invention, the lens may be provided with only a single rearward projection outwardly of the periphery of the optic. See, for example, lens 50 in FIGS. 4 and 5. A single tab 51, preferably unitary with lens body 18 extends radially outwardly of the periphery 19 of the lens body at a first peripheral portion 19a thereof. A projection 52 extends rearwardly from the tab 51 and is adapted to be pressed into the posterior capsule 16 under the influence of the position-fixation members 53 and 54, the latter of which is connected to and extends rearwardly from the tab 51. In this embodiment, position-fixation member 53 is preferably connected directly to the lens body at the peripheral region 19b thereof, which is diametrically opposed to the region 19a and thus, to the location of projection 52. Position-fixation member 53 acts to press the rear edge of lens body 18, at peripheral region 19b, toward the posterior capsule 16. Consequently, after implantation, the position-fixation members 53, 54 cooperate to form a stressed region in posterior capsule 16, i.e. between projection 52, on the one hand, and the rear edge of the rear surface 22 in the peripheral region 19b, on the other hand, and displace the central region 16a of the posterior capsule to the position thereof shown in FIG. 4, so as to create a space between the mid-portion 27' of the rear face 22 of the lens body and the posterior capsule portion 16a, which it overlies. The distance of such spacing, in such mid-region is sufficiently large to permit a safe laser capsulotomy to be performed subsequent to implantation.

The lens according to any of the embodiments of the present invention may be made of any material suitable for intraocular lenses, as, for example, polymethylmethacrylate.

Various modifications in structure and/or function may be made to the disclosed embodiments by one skilled in the art without departing from the scope of the invention as defined by the claims.

What is claimed is:

1. A posterior chamber intraocular lens intended for implantation in the capsule of an eye after extracapsular extraction, comprising:
   a medial, light-focusing, lens body having a rear face,
   a pair of discrete tab means extending generally radially outwardly from opposite peripheral portions of said lens body and integral therewith,
   position-fixation means extending from said tab means and cooperating with said lens body, for centering said lens within said chamber,
   a pair of projection respectively integral with said tab means at locations thereon closely adjacent to but radially outward of said opposite peripheral portions, respectively, of said lens body and extending rearwardly behind the plane containing said rear face of said lens body, each of said projections being shaped so as to make substantially only single point contact with said posterior capsule,
   said position-fixation means being adapted to act directly on said projection to press said projection against the posterior capsule for spacing a central portion of the posterior capsule away from said rear face a distance sufficiently large to safely allow a subsequent laser capsulotomy.

2. A lens according to claim 1 wherein said projections are effective to cause tension of the posterior capsule in the elongated region between said projections, when said lens is in implanted position, sufficient to tear the posterior capsule after only limited laser perforation of the capsule in said region.

3. A lens according to claim 1, wherein said tab means are at least not transparent to the passage of light therethrough.

4. A lens according to claim 1, wherein said position-fixation means comprise a pair of position-fixation members, respectively connected to and extending outwardly from said tab means.

5. A lens according to claim 3, wherein said tab means are translucent to the passage of light therethrough in direction generally parallel to the optical axis.

6. A lens according to claim 1, wherein said projections are effective to cause the region of the posterior capsule, between said projections, to assume the shape of an elongated groove, whose elongated central portion, at least, is out of contact with said rear face of the lens body.

7. A posterior chamber intraocular lens intended for implantation in an eye after extracapsular cataract extraction, comprising:
   a medial, light focusing, lens body having first and second opposed peripheral portions, a rear face having a mid-portion intermediate said first and second peripheral portion and said rear face having a rear edge at least in the region of said first and second peripheral portions,
   tab means attached only to said first peripheral portion of said lens body and extending outwardly beyond the periphery of the corresponding one of said rear edges thereof,
   position-fixation means cooperating with said lens body, for centering said lens body within said chamber, said position fixation means having a first position fixation member extending from said tab means, and
   a projection integral with said tab means at a location thereon outwardly of and closely spaced from the corresponding said rear edge and extending rearwardly behind the plane containing said mid-portion of said rear face of said lens body, said projection being shaped to make substantially only single point contact with the posterior capsule,
   said position-fixation means being adapted to press said projection and the rear edge of said second peripheral portion against the posterior capsule for forming an elongated stress region between said projection and said rear edge of said second peripheral portion and for spacing the posterior capsule, at least along such stress region thereof, away from said mid-portion of said rear face, when said lens is in implanted position, a distance sufficiently large to safely allow a subsequent laser capsulotomy.

8. A lens according to claim 7 wherein said tab means is at least translucent to the passage of light therethrough.

9. A lens according to claim 7 wherein said mid-portion of said rear face is generally planar.

10. A posterior chamber intraocular lens intended for implantation in the capsule of an eye after extracapsular extraction, comprising:
    a medial, light-focusing, lens body having a rear face,
    position-fixation means cooperating with said lens body, for centering said lens body within said chamber,
    projection means, integral with said position fixation means, at a location outwardly of the periphery of said lens body and extending rearwardly of a plane containing at least the mid-portion of said rear face and adapted to contact the posterior capsule outwardly of said periphery, in response to pressure exerted by said position-fixation means upon implantation of the lens in an eye,
    said projection means being shaped to make substantially only single point contact with the posterior capsule and the rearward length of said projection means being sufficiently large for spacing at least said mid-portion of said rear face away from the posterior capsule a distance sufficiently large to safely allow a subsequent laser capsulotomy.

* * * * *